US00PP22552P2

(12) United States Plant Patent
Smith

(10) Patent No.: US PP22,552 P2
(45) Date of Patent: Mar. 6, 2012

(54) ***CHRYSANTHEMUM* PLANT NAMED 'SYNJAC PINKA'**

(50) Latin Name: *Chrysanthemum×morifolium*
Varietal Denomination: Synjac Pinka

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 4 days.

(21) Appl. No.: 12/925,042

(22) Filed: Oct. 12, 2010

(51) Int. Cl.
*A01H 5/00* (2006.01)

(52) U.S. Cl. ..... Plt./287

(58) Field of Classification Search ..... Plt./291, Plt./287
See application file for complete search history.

*Primary Examiner* — June Hwu
(74) *Attorney, Agent, or Firm* — S. Matthew Edwards

(57) ABSTRACT

A new *Chrysanthemum* plant named 'Synjac Pinka' particularly distinguished by the small to medium sized flowers with light red-purple ray florets, dark yellow-green foliage, a garden *Chrysanthemum* with uniform ball-shaped plant habit and a natural flowering season of about mid-September.

1 Drawing Sheet

Latin name of the genus and species of the plant claimed: *Chrysanthemum×morifolium.*

Varietal denomination: 'Synjac Pinka'.

BACKGROUND OF THE NEW PLANT

The present invention comprises a new *Chrysanthemum,* botanically known as *Chrysanthemum×morifolium,* and hereinafter referred to by the variety name 'Synjac Pinka'.

'Synjac Pinka' is a product of a planned breeding program. The new cultivar has small to medium sized flowers with light red-purple ray florets, dark yellow-green foliage, a garden *Chrysanthemum* with uniform ball-shaped plant habit and a natural flowering season of about mid-September.

'Synjac Pinka' originates as a natural whole plant mutation of 'Yojacqueline', U.S. Plant Pat. No. 18,927 and was discovered in an outdoor controlled breeding trial and selected by the inventor as a single flowering plant within a population of the parent cultivar in Alva, Fla. in November 2006. The parent cultivar 'Yojacqueline' has two-toned pink ray florets with a faster natural flowering season response.

The first act of asexual reproduction of 'Synjac Pinka' was accomplished when vegetative cuttings were propagated from the initial selection in December 2006 in a controlled environment in Alva, Fla.

BRIEF SUMMARY OF INVENTION

Horticultural examination of plants grown from cuttings of the plant initiated in December 2006, and continuing thereafter, has demonstrated that the combination of characteristics as herein disclosed for 'Synjac Pinka' are firmly fixed and are retained through successive generations of asexual reproduction.

'Synjac Pinka' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6769). 'Synjac Pinka' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synjac Pinka' with colors being as true as possible with an illustration of this type. The photographic drawing shows a flowering potted plant of the new variety, and a close-up of the flowers.

DETAILED BOTANICAL DESCRIPTION

The plant descriptions and measurements were taken in Gilroy, Calif. in May 2010 under natural light. These plants were about 10 weeks old.

The aforementioned photographs were taken in Gilroy, Calif. in late October 2009 outdoors. These plants were approximately 12 weeks of age.

Color references are made to The Royal Horticultural Society Colour Chart (R.H.S.) 2001.

TABLE 1

DIFFERENCES BETWEEN THE NEW VARIETY 'SYNJAC PINKA' AND A SIMILAR VARIETY: 'YOURSULA' (U.S. Plant Pat. No. 13,641)

| | 'Synjac Pinka' | 'Yoursula' (U.S. Plant Pat. No. 13,641) |
|---|---|---|
| Ray floret quantity: | Fewer | More |
| Disc floret quantity: | Less | More |
| Plant size/habit: | Little larger/rounder | Smaller/less round |
| Natural flowering season response: | Couple days slower | Couple days faster |
| Shaded response: | Couple days faster | Couple days slower |

Plant:

*Form, growth and habit.*—Herbaceous decorative garden type; Stems upright and outwardly spreading, freely branching, strong and moderately vigorous growth habit.

*Plant height.*—12-14 cm.
*Plant height (inflorescence included).*—15-17.5 cm.
*Plant width.*—21-24 cm.
*Garden performance and tolerance to weather.*—Very good.

Roots:
*Number of days to initiate roots.*—4 days at about 22 degrees C.
*Number of days to produce a rooted cutting.*—10-12 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—Closest to RHS 147A.
*Lower surface.*—Lighter than RHS 147A.
*Mature, leaf color, upper surface.*—Closest to RHS 147A.
*Lower surface.*—Lighter than RHS 147A.
*Length.*—2.7-2.9 cm.
*Width.*—2.0-2.5 cm.
*Shape.*—Broadly ovate.
*Base shape.*—Attenuate.
*Apex shape.*—Mucronulate.
*Margin.*—Palmately; irregularly lobed; sometimes irregularly serrate.
*Texture, upper surface.*—Bifid T-shaped hairs.
*Lower surface.*—Bifid T-shaped hairs.
*Color of veins, upper surface.*—RHS 146C.
*Color of veins, lower surface.*—RHS 146C.
*Petiole color.*—RHS 146C.
*Length.*—0.4-0.9 cm.
*Diameter.*—0.2-0.3 cm.
*Texture.*—Bifid T-shaped hairs.

Stem:
*Quantity of main branches per plant.*—About 8-10.
*Color of stem.*—RHS 147B.
*Length of stem.*—8.0-9.0 cm.
*Diameter.*—0.3 cm.
*Length of internodes.*—0.5-0.8 cm.
*Texture.*—Bifid T-shaped hairs.
*Color of peduncle.*—Closest to RHS 147B.
*Length of peduncle.*—3-4.5 cm.
*Peduncle diameter.*—0.15-0.2 cm.
*Texture.*—Bifid T-shaped hairs.

Inflorescence:
*Type.*—Compositae type, solitary inflorescences (decorative-type) borne terminally above foliage, ray florets arranged acropetally on a capitulum.
*Natural season flowering.*—About mid-September.
*Quantity of inflorescences per plant.*—About 30-40 plus numerous buds.
*Lastingness of individual bloom on the plant.*—3-4 weeks.
*Fragrance.*—Very slightly spicy.

Bud (just when opening/showing color):
*Color.*—RHS 70B.
*Length.*—0.8-1.0 cm.
*Width.*—0.7-0.8 cm.
*Shape.*—Oblate.

Immature inflorescence:
*Diameter.*—2.5-3.0 cm.
*Color of ray florets, upper surface.*—RHS 75C with more RHS 70B and RHS 72B overlay.
*Lower surface.*—RHS 75B to RHS 75C.

Mature inflorescence:
*Diameter.*—3.5-4.0 cm.
*Depth.*—2.0 cm.
*Total diameter of 'disc'.*—0.2 cm.
*Receptacle height.*—0.5 cm.
*Receptacle diameter.*—1.2 cm.

Ray florets:
*Average quantity of florets.*—About 60 in numerous whorls.
*Color of florets, upper surface.*—RHS 75C with more RHS 70B overlay and less of RHS 72B overlay.
*Lower surface.*—RHS 75B to RHS 75C.
*Length.*—1.9-2.1 cm.
*Width.*—0.4 cm.
*Shape.*—Oblong to elliptical.
*Apex shape.*—Praemorse.
*Margin.*—Entire.
*Texture, upper surface.*—Papillose.
*Lower surface.*—Papillose.

Disc florets:
*Average quantity of florets.*—About 35.
*Color of florets.*—RHS 11B to RHS 11C with RHS 3A apex.
*Length.*—0.5 cm.
*Width.*—0.1 cm.
*Shape.*—Tubular, elongated.
*Apex shape.*—Acute, 5 pointed.

Phyllaries:
*Quantity.*—25-30.
*Color, upper surface.*—RHS 146A to RHS 146B.
*Lower surface.*—RHS 147B.
*Length.*—0.3-0.4 cm.
*Width.*—0.1-0.2 cm.
*Shape.*—Ovate.
*Apex shape.*—Acute.
*Based.*—Fused.
*Margins.*—Entire.
*Texture, upper surface.*—Glabrous.
*Lower surface.*—Bifid T-shaped hairs.

Reproductive organs:
*Pistil (presence on disc and ray florets).*—1.
*Length.*—0.4 cm.
*Style color.*—RHS 1B.
*Style length.*—0.3 cm.
*Stigma color.*—RHS 3A.
*Stigma shape.*—Bi-parted.
*Ovary color.*—Not observed.
*Stamens (presence on disc florets only).*—1.
*Color of filaments.*—RHS 1B.
*Length filaments.*—0.2 cm.
*Anther color.*—RHS 3A.
*Anther length.*—0.1 cm.
*Anther shape.*—Oblong.
*Color of pollen.*—Not observed.
*Pollen amount.*—Not observed.
*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Synjac Pinka' substantially as illustrated and described herein.

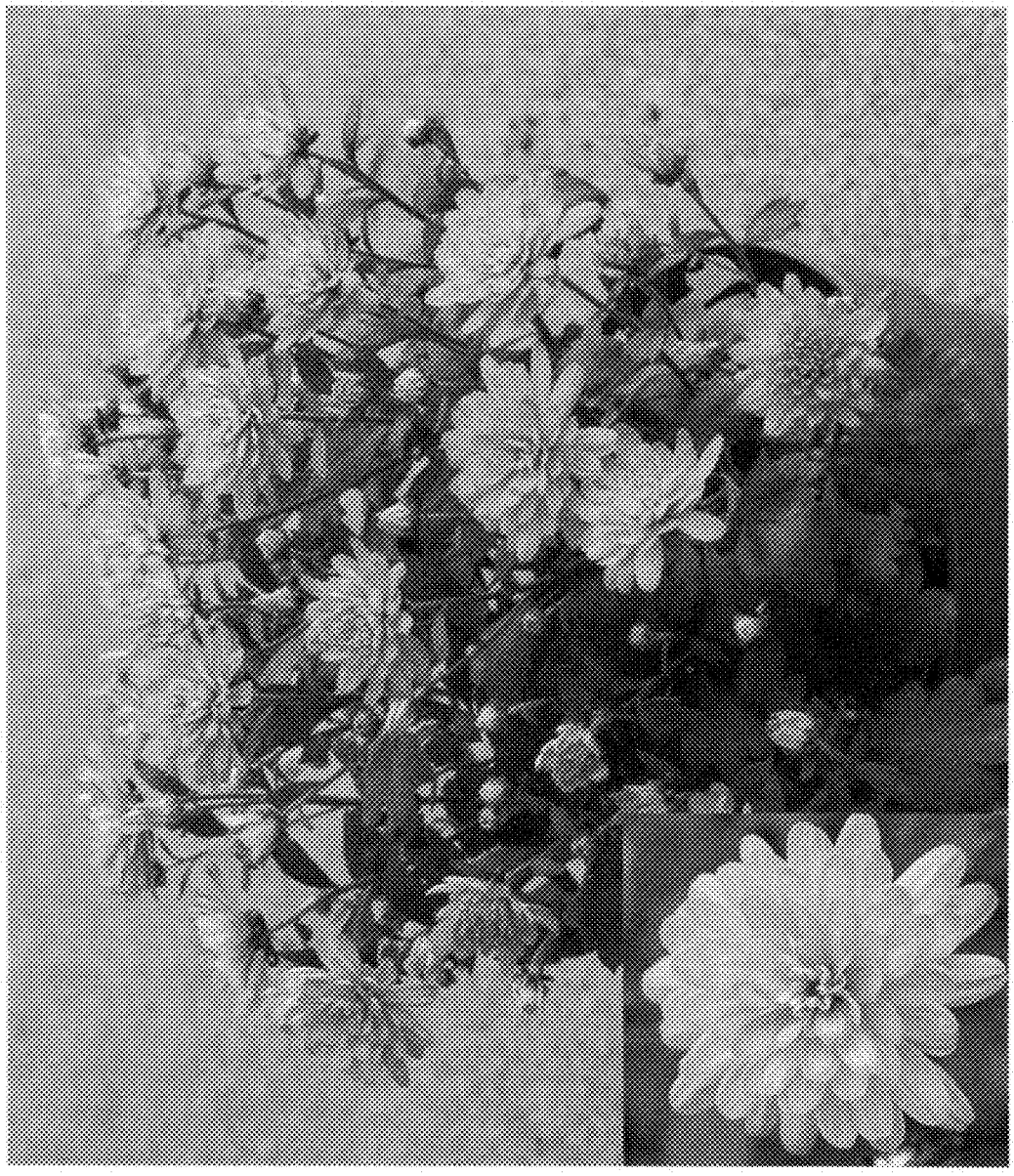

* * * * *